United States Patent [19]
Berg

[11] Patent Number: 5,851,362
[45] Date of Patent: Dec. 22, 1998

[54] SEPARATION OF 4-METHYL-2-PENTANOL FROM 3-METHYL-1-BUTANOL BY EXTRACTIVE DISTILLATION

[76] Inventor: Lloyd Berg, 1314 S. 3rd Ave., Bozeman, Mont. 59715

[21] Appl. No.: 863,668

[22] Filed: May 27, 1997

[51] Int. Cl.⁶ .............................. B01D 3/40; C07C 29/84
[52] U.S. Cl. ................................ 203/57; 203/58; 203/60; 203/68; 568/913
[58] Field of Search ................................. 203/68, 60, 58, 203/57; 568/913

[56] References Cited

U.S. PATENT DOCUMENTS

| | | | |
|---|---|---|---|
| 2,480,652 | 8/1949 | Hillman et al. | 203/57 |
| 2,706,707 | 4/1955 | Morrell et al. | 203/57 |
| 2,788,315 | 4/1957 | Morrell et al. | 203/57 |
| 5,196,094 | 3/1993 | Berg et al. | 203/58 |
| 5,207,876 | 5/1993 | Berg et al. | 203/60 |
| 5,401,366 | 3/1995 | Berg | 203/68 |
| 5,445,716 | 8/1995 | Berg | 203/57 |
| 5,658,436 | 8/1997 | Berg | 203/68 |

*Primary Examiner*—Virginia Manoharan

[57] ABSTRACT

4-Methyl-2-pentanol cannot be separated from 3-methyl-1-butanol by distillation because of the closeness of their boiling points. 4-Methyl-2-pentanol can be easily separated from 3-methyl-1-butanol by extractive distillation. Effective agents are dodecane, dimethylformamide and dimethylsulfoxide.

2 Claims, No Drawings

5,851,362

SEPARATION OF 4-METHYL-2-PENTANOL FROM 3-METHYL-1-BUTANOL BY EXTRACTIVE DISTILLATION

FIELD OF THE INVENTION

This invention relates to a method for separating 4-methyl-2-pentanol pentanol from 3-methyl-1-butanol using certain organic compounds as the agent in extractive distillation.

DESCRIPTION OF PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boll about twenty Celcius degrees or more higher than the highest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

The usual method of evaluating the effectiveness of extractive distillation agents is the change in relative volatility of the compounds to be separated. Table 1 shows the degree of separation or purity obtainable by theoretical plates at several relative volatilities. Table 1 shows that a relative volatility of at least 1.2 is required to get an effective separation by rectification

TABLE 1

Effect of Relative Volatility on Theoretical Stage Requirements.

| Separation Purity, | Relative Volatility | | | | | | | |
|---|---|---|---|---|---|---|---|---|
| Both Products (Mole Fraction) | 1.02 | 1.1 | 1.2 | 1.3 | 1.4 | 1.5 | 2.0 | 3.0 |
| | Theoretical Stages at Total Reflux | | | | | | | |
| 0.999 | 697 | 144 | 75 | 52 | 40 | 33 | 19 | 12 |
| 0.995 | 534 | 110 | 57 | 39 | 30 | 25 | 14 | 9 |
| 0.990 | 463 | 95 | 49 | 34 | 26 | 22 | 12 | 7 |
| 0.98 | 392 | 81 | 42 | 29 | 22 | 18 | 10 | 6 |
| 0.95 | 296 | 61 | 31 | 21 | 16 | 14 | 8 | 4 |
| 0.90 | 221 | 45 | 23 | 16 | 12 | 10 | 5 | 3 |

4-Methyl-2-pentanol and 3-methyl-1-butanol boil only two degrees apart and have a relative volatility of 1.1 and are difficult to separate by conventional rectification. Table 2 shows that to get 99% purity, 127 actual plates are required. With an agent giving a relative volatility of 1.4, only 35 actual plates are required.

TABLE 2

Theoretical and Actual Plates Required vs. Relative Volatility for 4-Methyl-2-pentanol-3-Methyl-1-butanol Separation

| Relative Volatility | Theoretical Plates Required At Total Reflux, 99 Purity | Actual Plates Required, 75% Eff. |
|---|---|---|
| 1.1 | 95 | 127 |
| 1.3 | 34 | 46 |
| 1.4 | 6 | 35 |

OBJECTIVE OF THE INVENTION

The object of this invention is to provide processes or methods of extractive distillation that will enhance the relative volatility of 4-methyl-2-pentanol to 3-methyl-1-butanol in their separation in a rectification column. It is a further object of this invention to identify effective azeotropic or extractive distillation agents that are stable and can be recycled.

SUMMARY OF THE INVENTION

The objects of this invention are provided by processes for the separation of 4-methyl-2-pentanol from 3-methyl-1-butanol which entails the use of certain organic compounds when employed as the agent in extractive distillation.

TABLE 3

Effective Extractive Distillation Agents For Separating 4-Methyl-2-pentanol From 3-Methyl-1-butanol

| Compounds | Relative Volatility |
|---|---|
| None | 1.1 |
| Dodecane | 1.3 |
| Dimethylformamide | 1.25 |
| Dimethylsulfoxide | 1.35* |

*Reverses the alcohols 3-Methyl-1-butanol/4-Methyl-2-pentanol

DETAILED DESCRIPTION OF THE INVENTION

I have discovered that certain organic compounds will effectively increase the relative volatility between 4-methyl-2-pentanol and 3-methyl-1-butanol during rectification when employed as the agent in extractive distillation. Table 3 summarizes the data obtained with these agents. They are dodecane, dimethylformamide and dimethylsulfoxide.

THE USEFULNESS OF THE INVENTION

The usefulness or utility of this invention can be demonstrated by referring to the data presented in Tables 1, 2, and 3. All of the successful agents show that 4-methyl-2-pentanol can be separated from 3-methyl-1-butanol by means of extractive distillation and that the ease of separation is considerable.

WORKING EXAMPLES

Example 1

Fifty grams of 4-methyl-2-pentanol- 3-methyl-1-butanol mixture and 50 grams of dodecane as the extractive agent were charged to a vapor-liquid equilibrium still and refluxed for four hours. The vapor composition was 68.1% 4-methyl-2-pentanol, 31.9% 3-methyl-1-butanol; the liquid composition was 73.3% 4-methyl-2-pentanol, 26.7% 3-methyl-1-butanol. This is a relative volatility of 3-methyl-1-butanol to 4-methyl-2-pentanol of 1.3.

Example 2

Fifty grams of 4-methyl-2-pentanol- 3-methyl-1-butanol mixture and 50 grams of dimethylsulfoxide as the extractive agent were charged to a vapor-liquid equilibrium still and refluxed for four hours. The vapor composition was 75.6% 4-methyl-2-pentanol, 24.4% 3-methyl-1-butanol; the liquid composition was 69.8% 4-methyl-2-pentanol, 2-pentanol, 30.2% 3-methyl-1-butanol. This is arrelative volatility of 4-methyl-2-pentanol to 3-methyl-1-butanol of 1.35.

I claim:

1. A method for recovering 3-methyl-1-butanol from a mixture of 3-methyl-1-butanol and 4-methyl-2-pentanol which consist essentially of distilling a mixture consisting of 3-methyl-1-butanol and 4-methyl-2-pentanol in the presence of an extractive agent, recovering the 3-methyl-1-butanol as overhead product and obtaining the 4-methyl-2-pentanol and the extractive agent as bottoms product, wherein said extractive agent is dodecane or dimethylformamide.

2. A method for recovering 4-methyl-2-pentanol from a mixture of 4-methyl-2-pentanol and 3-methyl-1-butanol which consists essentially of distilling a mixture consisting of 4-methyl-2-pentanol and 3-methyl-1-butanol in the presence of an extractive agent, recovering the 4-methyl-2-pentanol as overhead product and obtaining the 3-methyl-1-butanol and the extractive agent as bottoms product, wherein said extractive agent is dimethylsulfoxide.

* * * * *